United States Patent [19]
Magni

[11] Patent Number: 5,250,573
[45] Date of Patent: Oct. 5, 1993

[54] GLUTARALDEHYDE-BASED STERILISING COMPOSITION OF ANTIBACTERIAL AND ANTIMYCOTIC ACTIVITY, IN AN AQUEOUS VEHICLE

[75] Inventor: Luigi F. Magni, Milan, Italy
[73] Assignee: Germo S.p.A., Italy
[21] Appl. No.: 268,990
[22] Filed: Nov. 9, 1988

Related U.S. Application Data

[63] Continuation-in-part of Ser. No. 71,939, Jul. 9, 1987, abandoned.

[51] Int. Cl.$^5$ ................ A61K 31/11; A61K 31/045
[52] U.S. Cl. .................... 514/701; 514/724; 514/728
[58] Field of Search ............ 252/106, 142, 143, 170; 514/701, 724, 728

[56] References Cited

U.S. PATENT DOCUMENTS

| | | | |
|---|---|---|---|
| 3,016,328 | 1/1962 | Pepper et al. | 424/127 |
| 3,057,775 | 10/1962 | Rendon | 424/75 |
| 3,812,450 | 5/1974 | Simovits, Jr. et al. | 339/128 |
| 3,912,450 | 10/1975 | Boucher | 21/54 A |
| 3,917,850 | 11/1975 | Boucher | 424/333 |
| 4,082,852 | 4/1978 | Heiss | 424/317 |
| 4,103,001 | 7/1978 | Schattner | 424/660 |
| 4,208,404 | 6/1980 | Cowan | 424/153 |
| 4,336,270 | 6/1982 | Muntwyler | 424/347 |
| 4,469,614 | 9/1984 | Martin | 252/106 |
| 4,690,772 | 9/1987 | Tell et al. | 252/106 |

FOREIGN PATENT DOCUMENTS 564947  8/1975  European Pat. Off. ............ 424/333

Primary Examiner—Zohreh A. Fay
Attorney, Agent, or Firm—Parkhurst, Wendel & Rossi

[57] ABSTRACT

A sterilising composition of antibacterial and antimycotic activity possessing considerable stability with time, comprising glutaraldehyde, an alkyl-, aryl- or halogen-substituted phenol, a non-ionic surface-active agent and preferably an alkanol of 2-5 carbon atoms, in an aqueous vehicle, at a pH of between 3.5 and 5.5.

3 Claims, No Drawings

GLUTARALDEHYDE-BASED STERILISING COMPOSITION OF ANTIBACTERIAL AND ANTIMYCOTIC ACTIVITY, IN AN AQUEOUS VEHICLE

This is a continuation-in-part of application Ser. No. 07/071,939 filed Jul. 9, 1987, now abandoned.

This invention relates to an aqueous chemical composition of considerable sporicidal, virucidal, fungicidal and bactericidal power suitable for use as a desinfectant sterilising at ambient temperature and possessing considerable stability with time. The disinfecting and sterilisation of equipment and devices used in the diagnostic and therapeutic field such as equipment for dental and hemodialysis use, and the disinfecting of treatment environments and the clothes of the patient or assisting personnel, require the use of products which as far as possible satisfy the following requirements:
   wide range of action
   short contact time
   low toxicity
   moderate cost
   suitability for use at ambient temperature
   absence of corrosion of the treated objects, especially if metallic.

Considerable sporicidal power is also of fundamental importance in obtaining reliable and total sterilisation.

A composition which has been widely used in recent years is one based on glutaraldehyde in aqueous solution.

This product presents its maximum activity at basic solution pH, whereas at acid pH its activity is very low, and in particular its sporicidal power is practically non-existent.

On the other hand, when in solution at basic pH, glutaraldehyde has a very limited stability with time because it easily undergoes polycondensation with the formation of a polycondensate without activity. Compositions based on glutaraldehyde in aqueous solution have been formed comprising a buffer system in order to obtain solutions with a strictly controlled pH which is not excessively basic, for example between 7 and 7.4. Aqueous solutions of glutaraldehyde at acid pH which are stable and possess good bactericidal power have also been formed by adding non-ionic surface-active agents to the solution.

The present invention provides a new disinfectant and sterilising composition consisting of an aqueous solution of glutaraldehyde at pH 3.5-5.5 which in addition to glutaraldehyde also contains the following essential components:

a) an alkyl-, aryl-, or halogen-substituted phenol or a thiobisphenol, in a quantity of 0.1-0.75 parts by weight per part by weight of glutaraldehyde;

b) a non-ionic surface-active agent of polyethoxylated type, in a quantity of 0.3-25 parts by weight per part by weight of glutaraldehyde, preferably of 0.5-5.

In the compositions according to the invention the use of non-ionic surface-active agents of the type above defined is essential in order to obtain a final product in form of a limpid and homogeneous liquid stable in storage at considered pH range 3.5-5.5. If in similar compositions anionic surfactants are used instead of non-ionic surfactants according to the invention, one obtains a turbid liquid having tendency to separate components. The clouding and subsequent components separation can occur also after dilution with water of the concentrated product.

The presence of a linear or branched alkanol of 2-5 carbon atoms is also preferred in a quantity of up to 30 parts by weight and in particular from 3 to 28 parts by weight per part by weight of glutaraldehyde, and more preferably from 5 to 10.

The composition according to the invention can be prepared as commercial product having high concentration (up to 20% by w.) of glutaraldehyde. This product is diluted with water at the moment of the use in order to obtain a concentration of glutaraldehyde proper for the intended use as specified in the following.

A particularly useful commercial composition is the following:

| | |
|---|---|
| glutaraldehyde | 2% by weight |
| phenol | 1% by weight |
| surface-active agent | 3% by weight |
| alcohol | 16% by weight |

A particularly suitable alcohol for the compositions of the present invention is isopropanol.

The non-ionic surface-active agent of polyethoxylated type is chosen from the following:
   alkyphenol with the alkyl of 8-9 carbon atoms, ethoxylated with 9-12 moles of ethylene oxide (EtO), and in particular ethoxylated nonyphenol;
   linear aliphatic alcohol of 11-16 carbon atoms, ethoxylated with 9-12 EtO.

The following phenols can be advantageously used in the compositions according to the invention:
   o, phenylphenol
   2,4,5-trichlorophenol
   2,2'-dihydroxy-5,5'-dichloro-diphenylmethane (chlorophene)
   2,2'-dihydroxy-5,5'-dichloro-diphenylmonosulphide (fenticlor)
   hexachloro-dihydroxy-diphenylmethane (hexachlorophene).

The concentration of the disinfectant sterilising composition according to the invention in the aqueous solution varies according to the particular type of disinfection or sterilisation for which it is to be used.

A concentration corresponding to 0.2% by weight of glutaraldehyde in the aqueous solution is suitable for the ambient-temperature sterilisation of diagnostic and surgical instruments in general within a time of 20 minutes. A concentration corresponding to 0.1% of glutaraldehyde is suitable for the ambient-temperature sterilisation of fibre optic equipment within a time of 10 minutes. A concentration of 0.02 preferably 0.06% is suitable for the aseptic preservation of instruments. The composition according to the invention can be prepared in the form of a high-concentration aqueous solution for dilution at the moment of use to the degree of dilution suitable for the specific application. Because of the high miscibility of the components with water, formulations can be prepared with a glutaraldehyde concentration of up to 20% by weight. The other ingredients are proportional to the glutaraldehyde present, in the aforesaid proportions. Compositions according to the invention in the form of a concentrated aqueous solution, and in particular containing 2% of glutaraldehyde by weight, are very stable with time, lasting at least 24 months.

They are also active in the presence of blood, proteins and organic materials. They can be advantageously used for sterilising and disinfecting the following instruments and articles:
- diagnostic apparatus
- endoscopy and urology apparatus (gastroscopes, cystoscopes, vascular and invasive probes)
- apparatus for anesthesia
- aerosol apparatus
- hemodialysis apparatus and microdiffusers
- dentistry apparatus
- plates for mesotherapy
- stainless steel, glass and rubber instruments.

An example of the preparation of the composition according to the invention is described hereinafter by way of illustration only.

EXAMPLE 4 g of 50% glutaraldehyde are mixed with 20 ml of isopropanol and 30 g of distilled water. Separately, 1 g of o.phenylphenol, 3 g of nonylphenol polyethoxylated with 10 moles of EtO per mole, and 40 g of distilled water are mixed together at 40° C. The two solutions are mixed together and made up to 100 g with distilled water.

Bactericidal and sporicidal activity

The three following solutions were prepared, the first of which represents a composition according to the known art. The percentages are by weight.

A) 2% glutaraldehyde + 0.25% non-ionic surface-active agent, in water

B) 2% glutaraldehyde, 1% o.phenylphenol, 3% non-ionic surface-active agent, in water C) 2% glutaraldehyde, 1% o.phenylphenol, 3% non-ionic surface-active agent, 16% isopropanol.

Micro-organisms:

For our tests, 18 hour broth cultures of the following micro-organisms forming part of our collection and originating from various pathological material were used.

As gram positive germs:
- S. aureus
- Streptococcus spp.
- Bacillus subtilis (and its spores)

As gram negative germs:
- Escherichia coli
- Klebsiella pneumoniae
- Serratia Marcescens
- Salmonella typhi
- Pseudomonas aeruginosa
- Proteus indole negative
- Proteus indole positive As mycetes:
- Candida albicans
- Aspergillus spp.

Minimum inhibiting concentrations:

Broth cultures were prepared in Todd Hewitt broth (Difco) for the streptococci, in Mueller Hinton broth (Difco) for the other gram positive and gram negative bacterial strains, and in Sabouraud broth for the mycetes, and these were incubated at 37° C. for 18 hours in the case of the bacteria and at 37° C. for 48 or 72 hours in the case of the mycetes.

After suitable dilution ($10^{-3}$), a quantity of 0.1 ml of each dilution was inoculated into Todd Hewitt, Mueller Hinton or Sabouraud broth respectively, containing dilutions on a doubling scale of the three solutions A, B and C being studied.

The inoculant consisted of $10^5$ CFUs (colony forming units).

After incubation at 37° C. for 18 hours or for 72 hours for the mycetes, the MIC (minimum inhibiting concentration) was determined as the lowest antibiotic concentration able to completely inhibit the growth of the germ under examination.

Minimum bactericidal concentrations:

Subcultures on suitable growth culture media to which agar had been added were prepared from the tubes containing the minimum inhibiting disinfectant concentrations and from the two tubes containing the two greater disinfectant concentrations on the doubling scale.

These inoculated culture media were then incubated at the appropriate temperatures for the required times.

The reading was taken in CFUs (colony forming units).

The minimum bactericidal concentration was considered to be that disinfectant concentration for which the subculture was sterile.

Determination of contact times:

Subcultures of four chosen test micro-organisms were prepared at determined time intervals from concentrations on a doubling scale of the three solutions under examination.

The chosen micro-organisms were:
- S. aureus
- B. subtilis
- P. aeruginosa
- C. albicans The chosen time intervals were 30 seconds, 1, 2, 5, 10, 20 and 30 minutes from the preparation of the starting culture.

After preparing these subcultures the inoculated tubes were incubated at 37° C. for the appropriate times.

The reading was taken by checking the turbidity attributable to any growth which had taken place.

Conclusive results and considerations:

Minimum inhibiting concentrations

The values obtained as minimum inhibiting concentrations of the tested micro-organisms are given in the accompanying Tables 1, 2 and 3.

Good synergic action of the three active principles examined can be deduced from these. In this respect, the values obtained improved continuously in passing from solution A to solution B and then to solution C.

Whereas the MIC values for solutions A and B are approximately ¼ and ⅛, a considerably lower MIC is obtained for solution C, namely down to 1/64 of the mother solution.

Minimum bactericidal concentrations

All the MIC values obtained for the germs chosen for the test can be superimposed on the MBC values. This ensures rapid bactericidal, fungicidal and sporicidal activity of the solutions, as can be seen from Table 4.

Contact times

The values given as contact times necessary for killing the tested micro-organisms are shown in the accompanying Tables 5, 6, 7 and 8.

The contact times obtained decrease in progressing through the three respective solutions.

TABLE 1

| Minimum inhibiting concentrations for gram positive germs | | | |
|---|---|---|---|
| Micro-organism | Solution A | Solution B | Solution C |
| S. aureus 1 | ¼ | ⅛ | 1/16 |
| S. aureus 2 | ¼ | ⅛ | 1/16 |
| S. aureus 3 | ¼ | ⅛ | 1/16 |
| Streptococcus 1 | ¼ | ⅛ | 1/32 |

TABLE 1-continued

Minimum inhibiting concentrations for gram positive germs

| Micro-organism | Solution A | Solution B | Solution C |
|---|---|---|---|
| Streptococcus 2 | ⅛ | 1/16 | 1/32 |

TABLE 2

Minimum inhibiting concentrations for gram negative germs

| Micro-organism | Solution A | Solution B | Solution C |
|---|---|---|---|
| Escherichia coli | ⅛ | ⅛ | ⅛ |
| Klebsiella pneumoniae | ⅛ | ⅛ | 1/32 |
| S. marcescens | ⅛ | ⅛ | 1/32 |
| S. typhi | ⅛ | ⅛ | 1/32 |
| P. aeruginosa | ⅛ | ⅛ | 1/64 |
| P. ind+ | ⅛ | ⅛ | 1/64 |
| P. ind− | ⅛ | ⅛ | 1/32 |

TABLE 3

Minimum inhibiting concentrations for sporogenic germs

| Micro-organism | Solution A | Solution B | Solution C |
|---|---|---|---|
| B. subtilis 1 | ⅛ | ⅛ | 1/16 |
| B. subtillis 2 | ⅛ | 1/16 | 1/64 |
| B. subtillis 3 | ⅛ | 1/32 | 1/64 |
| Spores | ⅛ | ⅛ | 1/32 |
| | ⅛ | ⅛ | 1/16 |

TABLE 4

Minimum concentrations for mycetes

| Micro-organism | Solution A | Solution B | Solution C |
|---|---|---|---|
| C. albicans 1 | ⅛ | ⅛ | 1/16 |
| C. albicans 2 | ⅛ | ⅛ | 1/16 |
| C. albicans 3 | ⅛ | 1/16 | 1/64 |

TABLE 5

Contact times for gram positive germs

| Micro-organism | Solution A | Solution B | Solution C |
|---|---|---|---|
| S. aureus 1 | 2 min | 1 min | 30 sec |
| S. aureus 2 | 5 min | 2 min | 30 sec |
| S. aureus 3 | 10 min | 5 min | 1 min |
| Streptococcus 1 | 2 min | 2 min | 30 sec |
| Streptococcus 2 | 2 min | 1 min | 30 sec |

TABLE 6

Contact times for gram negative germs

| Micro-organism | Solution A | Solution B | Solution C |
|---|---|---|---|
| Escherichia coli | 5 min | 2 min | 1 min |
| Klebsiella pneum. | 10 min | 5 min | 2 min |
| S. marcescens | 10 min | 2 min | 1 min |
| S. typhi | 10 min | 2 min | 2 min |
| P. aeruginosa | 5 min | 2 min | 30 sec |
| P. ind.+ | 2 min | 1 min | 30 sec |
| P. ind.− | 2 min | 30 sec | 30 sec |

TABLE 7

Contact times for sporogenic germs and their spores

| Micro-organism | Solution A | Solution B | Solution C |
|---|---|---|---|
| B. subtilis 1 | 10 min | 5 min | 2 min |
| B. subtilis 2 | 5 min | 1 min | 30 sec |
| B. subtilis 3 | 5 min | 2 min | 30 sec |
| Spores | 20 min | 10 min | 5 min |
| | 30 min | 10 min | 2 min |
| | 30 min | 20 min | 10 min |

TABLE 8

Contact times for mycetes

| Micro-organism | Solution A | Solution B | Solution C |
|---|---|---|---|
| C. albicans 1 | 20 min | 20 min | 10 min |
| C. albicans 2 | 10 min | 10 min | 2 min |
| C. albicans 3 | 30 min | 10 min | 5 min |

Comparison tests a) 4 g. of 50% glutaraldehyde are mixed with 20 ml of isopropanol and 30 g of H20. Separately 1 g of o.phenylphenol, 7 g of anionic surfactant Texapon T25 of the firm Henkel (sodium laurylether sulphate at 25% concentration in water) and 40 g $H_2O$ are mixed together at 40 C. The two solutions are mixed together and made up to 100 g with distilled water. A turbid product is obtained which shows a pH of 3.5 and in storage separates some components.

b) Test a) was repeated with the difference that the anionic surfactant was Texapon T42 of the firm Henkel (sodium salt of the sulphate of lauryl alcohol ethoxylated with two mols of ethylene oxide).

The turbid product obtained has pH of 5.5 and in storage separates some components.

I claim:

1. A disinfectant and sterilizing aqueous glutaraldehyde solution having a pH of 3.5 to 5.5 containing 0.02 to 0.2% by weight of glutaraldehyde,
   an alkyl-, aryl- or halogen-substituted phenol or thiobisphenol, present in an amount of 0.1 to 0.75 parts by weight per part by weight of glutaraldehyde,
   a nonionic surface active agent which is an alkyl phenol with a $C_8$–$C_9$ alkyl and ethoxylated with 9 to 12 moles of ethylene oxide or a linear $C_{11}$–$C_{16}$ aliphatic alcohol ethoxylated with 9 to 12 moles of ethylene oxide, present in an amount of 0.3 to 25 parts by weight per part by weight of glutaraldehyde, and
   a linear or branched $C_2$–$C_5$ alkanol, present in an amount of 3 to 28 parts by weight per part of weight of glutaraldehyde.

2. A composition as claimed in claim 1, obtained by diluting with water the aqueous composition containing:

| | |
|---|---|
| glutaraldehyde | 2% by weight |
| phenol | 1% by weight |
| non-ionic surface-active agent | 3% by weight |
| alcohol | 16% by weight |

3. A composition as claimed in claim 1, wherein the phenol is chosen from:
   o.phenylphenol
   2,4,5-trichlorophenol
   2,2'-dihydroxy-5,5'-dichloro-diphenylmethane
   2,2'-dihydroxy-5,5'-dichloro-diphenylmonosulphide
   2,2'-dihydroxy-3,3',5,5',6,6'-hexachloro-diphenylmethane.

* * * * *